(12) United States Patent
Armstrong et al.

(10) Patent No.: US 7,727,950 B2
(45) Date of Patent: Jun. 1, 2010

(54) METHODS AND REAGENTS FOR ASSAYING PROTEIN KINASE ACTIVITY

(75) Inventors: Chris Armstrong, Dundee (GB); Philip Cohen, Dundee (GB)

(73) Assignee: The University of Dundee, Dundee (GB)

( * ) Notice: Subject to any disclaimer, the term of this patent is extended or adjusted under 35 U.S.C. 154(b) by 658 days.

(21) Appl. No.: 10/510,875

(22) PCT Filed: Mar. 26, 2003

(86) PCT No.: PCT/GB03/01286

§ 371 (c)(1),
(2), (4) Date: Jun. 27, 2005

(87) PCT Pub. No.: WO03/087400

PCT Pub. Date: Oct. 23, 2003

(65) Prior Publication Data

US 2006/0073575 A1    Apr. 6, 2006

(30) Foreign Application Priority Data

Apr. 9, 2002    (GB) ................... 0208104.0

(51) Int. Cl.
- *A61K 38/00* (2006.01)
- *A61K 38/04* (2006.01)
- *A61K 38/10* (2006.01)
- *C07K 16/00* (2006.01)
- *G01N 33/53* (2006.01)

(52) U.S. Cl. .............. 514/2; 514/12; 514/13; 514/14; 514/15; 514/16; 530/300; 530/324; 530/325; 530/326; 530/387.1; 530/388.1; 435/7.1

(58) Field of Classification Search ........... None
See application file for complete search history.

(56) References Cited

FOREIGN PATENT DOCUMENTS

| WO | WO 00/14536 | | 3/2000 |
|---|---|---|---|
| WO | WO 00 14536 | * | 3/2000 |
| WO | WO 02/27017 | | 4/2002 |

OTHER PUBLICATIONS

Albert et al. Molecular Biology of the Cell, 4th ed., 2002, pp. 176-178.*
Brown et al., Nature, 369:756-758(1994).
Cross et al., Nature, 378:785-789(1995).
Davies et al., Biochem. J., 351:95-105(2000).
Flowtow et al., J. Biol. Chem., 265:14264-14269(1990).
Kobayashi et al., Biochem. J., 339:319-328(1999).
Leighton et al., FEBS Letters, 375:289-293(1995).
Liu et al., Cell, 66:807-815(1991).
Michael Morin, Oncogene, 19:6574-6583(2000).
Pinna et al., Biochimica et Biophysica Acta, 1314:191-225(1996).
Parker et al., J. Biomolecular Screening, 5:77-88(2000).
Ross et al., Biochem. J., 366:977-981(2002).
Stokoe et al, Biochem. J. 296:843-849(1993).

* cited by examiner

*Primary Examiner*—Anish Gupta
*Assistant Examiner*—Julie Ha
(74) *Attorney, Agent, or Firm*—Knobbe Martens Olson & Bear LLP

(57) ABSTRACT

A kit of parts comprising two or more protein kinase substrate polypeptides, each said substrate polypeptide comprising a specificity conferring portion (which is different for each said kinase substrate polypeptide) and a phosphorylatable portion, wherein the phosphorylatable portions of each polypeptide are capable of being bound in a phosphorylation state-sensitive manner by the same specific binding partner, for example and antibody preparation, and wherein the said specific binding partner is not an antibody specific for phosphotyrosine, phosphoserine or phosphothreonine. The phosphorylatable portion preferably comprises the amino acid sequence LSFAEPG.

15 Claims, 2 Drawing Sheets

Figure 1:
Figure 1:
Figure 1:
Figure 1:
Figure 1:

| 10 ng | 100 ng | Competitor peptide |
|---|---|---|
|  | | None |
| | | LpSFAEPG (SEQ ID NO:7) |
|  | | RARTLSFAEPG (SEQ ID NO:16) |
| | | RARTLpSFAEPG (SEQ ID NO:26) |
|  | | KKLNRTLSFAEPG (SEQ ID NO:13) |
| | | KKLNRTLS*FAEPG (SEQ ID NO:31) |
|  | | RRRLSFAEPG (SEQ ID NO:4) |
|  | | RRRLpSFAEPG (SEQ ID NO:27) |

METHODS AND REAGENTS FOR ASSAYING PROTEIN KINASE ACTIVITY

The present invention relates to methods and reagents useful in assaying protein kinase activity and screening for modulators of protein kinase activity, in particular serine/threonine protein kinases The attachment and removal of phosphate from proteins catalysed by protein kinases and protein phosphatases regulates nearly all aspects of cell life. In recent years it has become apparent that abnormal protein phosphorylation is a cause or consequence of many diseases and pathological conditions including, arthritis, cancer diabetes, heart disease, hypertension and stroke. For this reason, the development of drugs that modulate the activities of various protein kinases and phosphatases selectively has become a major priority for the pharmaceutical industry. This interest has been heightened by the discovery that cyclosporin, the immunosuppressant drug that permitted the widespread use of organ transplantation, inhibits a protein phosphatase (protein phosphatase 2B/calcineurin) [1] and that its successor, rapamycin, inhibits a protein kinase (the "mammalian target of rapamycin", mTOR) [2]. Furthermore, Gleevec (STI 571), an inhibitor of the abl tyrosine kinase, was approved for clinical use by the U.S. Food and Drug Administration in May 2001. This compound has shown impressive efficacy for the treatment of Chronic Myelogenous Leukaemia (CML), a disease in which abl is converted to a constitutively active form by a chromosomal rearrangement (reviewed in [3]). Gleevec is the first drug to be developed by targetting a specific protein kinase for inhibition.

One of the first steps in the drug discovery process (exemplified in relation to protein kinases) involves screening compound libraries to identify 'lead' inhibitors of particular protein kinases. Traditionally, such "high throughput screening" for protein kinase inhibitors has involved strategies that measure the effect of compounds on the incorporation of radiolabelled phosphate ($^{32}P$ and $^{33}P$) into peptide and protein substrates. However, one of the major drawbacks of such radioactive assay formats is that compound libraries are becoming extremely large (>1 million entities), as a consequence of advances in combinatorial chemistry and the integration of compound libraries resulting from mergers and acquisitions. Consequently, high levels of radioactivity are required to run these assays and the industry has increasingly looked to develop alternative non-radioactive assay formats. One potentially attractive non-radioactive assay is to use phospho-specific antibodies that recognise the product of the kinase reaction. The simplest approach would be to use phospho-specific antibodies that recognise peptides that contain either a phosphoserine, phosphothreonine or phosphotyrosine residue. Indeed, such antibodies have been extremely successful for the assay of protein tyrosine kinases. However, the development of equivalent assays for serine/threonine-specific protein kinases or phosphatases has not been possible because sufficiently good antibodies that recognise peptides containing phosphoserine or phospho-threonine have not yet been achieved. It has therefore been necessary to develop separate phospho-specific antibodies for each phosphorylated substrate.

We provide synthetic peptide substrates that are considered to be excellent substrates for a large number of different protein kinases. These peptides share a common epitope (for example a seven residue epitope) that includes the site of phosphorylation and which is the target for an effective phospho-specific antibody. Using such substrates, many protein kinases can be screened using a common format. For example, the substrates may be used in identifying modulators of protein kinases, or in identifying or characterising protein kinases.

Many protein kinases phosphorylate residues, for example serine residues, that lie in particular amino acid motifs. For example, PKA and PKG phosphorylate serines that lie in Arg-Arg-Arg-Xaa-Ser-sequences [5], while PKB, SGK, MAPKAP-K1 and S6K1 phosphorylate serines that lie in Arg- (or Lys)-Xaa-Arg-Xaa-Xaa-Ser-motifs [6, 7]. On the other hand, MAPKAP-K2, MAPKAP-KIII and CaMKII recognise Hyd-Xaa-Arg-Xaa-Xaa-Ser-motifs, where Hyd is a bulky hydrophobic residue [8]. In addition, nearly all of these protein kinases prefer a bulky hydrophobic residue immediately C-terminal to the site of phosphorylation.

Surprisingly, we have found that peptides that share a common C-terminal epitope are phosphorylated efficiently by many different protein kinases, which fall into several different kinase subfamilies. Indeed, in many cases, is such a peptide is phosphorylated as efficiently, and sometimes even more efficiently, than the substrates in routine use for the assay of a particular protein kinase. This was unexpected because the peptides would not be expected to have an appropriate conformation and because the prior art describes specific peptides for specific kinases (see, for example [4]). Further, the C-terminal epitope can be used to generate a single phospho-specific antibody capable of assaying many protein kinases. C-terminal epitope sequences were found to be preferable to N-terminal epitope sequences, which were found to be less optimal.

In particular, we have designed and characterised generic peptides (shown in Table 1 of Example 1) that contain a common seven residue epitope related to the sequence surrounding the serine in glycogen synthase kinase 3 that is phosphorylated by PKB [9]. Such an epitope may be particularly suitable for assaying protein kinases that do not have a strong sequence preference C-terminal of the phosphorylated residue, for example members of the PKA family (including, for example, PKG, ROCKII and isoforms of PKC), PKB family (including, for example, SGK, MSK, MAPKAP-K1 and S6K and isoforms of PKB or MAPKAP-K2 family (including, for example, MAPKAP-K3, PRAK, CHK1, CHK2, AMPK and CaMKII) or CK1 isoforms and subfamily.

We consider that the particular three peptides discussed in Example 1 and Table 1 can be used as substrates by all the closely related isoforms of the protein kinases studied in Example 1, and also by most, if not all, of the other members of the same kinase subfamilies (for example members of the PKB, PKA or MAPKAP-K2 families, as discussed above).

We also consider that additional peptides with the same C-terminal epitope may be used to assay other protein kinases that recognise a specific motif N-terminal to the site of phosphorylation. For example, CK1 (previous called casein kinase1) phosphorylates serine residues that lie three residues C-terminal to another phosphoserine residue [10]. It may therefore phosphorylate peptides of the type Xaa-pSer-Xaa-Leu-Ser-Phe-Ala-Glu-Pro-Gly (ie having the same C-terminal epitope as the peptides investigated in Example 1). We therefore consider that at least 50 and probably more than 100 protein kinases may be assayed using peptides having this epitope.

Although PKC could be assayed perfectly well using a peptide comprising the said epitope (Table 1), this substrate was inferior to other substrates that have been used to assay this protein kinase. This is considered to be because PKC prefers basic residues C-terminal to the site of phosphorylation, which are not present in the epitope, in addition to basic residues N-terminal to the site of phosphorylation [5]. A preferred epitope for isoforms of PKC and related protein kinases, such as AGC family members may comprise or consist of the seven amino acids starting with the serine of the peptide substrate RRRLSFAEPG (SEQ ID NO: 4).

Further, in view of the results presented herein, protein kinases that have a stringent requirement for a particular motif or residue C-terminal to the site of phosphorylation may be assayed using substrate peptides in which the shared epitope is N-terminal of the specificity-conferring portion of the peptide. For example, MAP kinases and cyclin-dependent protein kinases have an absolute requirement for a proline residue immediately C-terminal to the site of phosphorylation [5], which is a negative determinant for the protein kinases tested in Example 1. Similarly CK2 requires several consecutive acidic residues C-terminal to the site of phosphorylation, while the DNA-dependent protein kinase requires a C-terminal glutamine [5]. However, in view of the results presented herein, a second series of peptide substrates with a common N-terminal epitope are considered to be useful in assaying many protein kinases that require a specific C-terminal motif for phosphorylation.

A first aspect of the invention provides a kit of parts comprising two or more protein kinase substrate polypeptides, each said substrate polypeptide comprising a specificity conferring portion (which is different for each said kinase substrate polypeptide) and a phosphorylatable portion, wherein the phosphorylatable portions of each polypeptide are capable of being bound in a phosphorylation state-sensitive manner by the same specific binding partner, for example an antibody preparation, and wherein the said specific binding partner is not an antibody specific for phosphotyrosine, phosphoserine or phosphothreonine. It is strongly preferred that the phosphorylatable portions of the polypeptides have identical amino acid sequences though this is not essential so long as the phosphorylatable portions share a common phosphorylation state-sensitive binding region (for example, an epitope) which extends beyond merely the phosphorylated residue. Thus, the binding partner, for example antibody preparation, is not an antibody preparation raised/selected against phosphoserine, phosphothreonine or phosphotyrosine (as opposed to being raised/selected against a longer amino acid sequence comprising a phosphoserine, phosphothreonine or phosphotyrosine residue).

A further aspect of the invention provides a kit of parts comprising two or more polypeptides, wherein the polypeptides are two or more protein kinase substrate polypeptides as defined in relation to the kit of parts of the first aspect of the invention in which the phosphorylatable portion of at least one said polypeptide is phosphorylated. Such phosphorylated polypeptides may be useful as substrates for protein phosphatases.

It is preferred that each said substrate polypeptide is of less than 40, 30, 20, 19, 18, 17, 16, 15, or 14 amino acids in length. It is particularly preferred that the substrate polypeptide is 13, 12, 11, 10 or 9 amino acids in length. The smaller peptides may be preferred on grounds of cost and convenience.

The protein kinase substrate polypeptide is a substrate for a protein kinase, ie is capable of being phosphorylated by a protein kinase, preferably a serine/threonine protein kinase. The phosphorylatable portion of the substrate polypeptide comprises a tyrosine, or more preferably a serine or threonine, residue that is phosphorylatable by the protein kinase. The specificity conferring portion (which may overlap with the phosphorylatable portion, for example may encompass the residue immediately N-terminal and/or C-terminal of the phosphorylatable tyrosine, serine or threonine residue) comprises an amino acid sequence that corresponds to a consensus sequence for phosphorylation by the protein kinase. The tyrosine, serine or threonine residue (for example when phosphorylated) forms part of an epitope against which a binding partner, for example an antibody preparation, may be raised/selected.

It is considered that the principle of a substrate polypeptide comprising a specificity conferring portion and a common phosphorylatable portion applies to tyrosine protein kinases as well as serine/threonine protein kinases. However, it is considered that the benefits provided may be more significant in relation to serine/threonine protein kinases in view of the existence of high affinity/specificity anti-phosphotyrosine antibodies, in contrast to the lack of high affinity/specificity anti-phosphoserine or anti-phosphothreonine antibodies.

It is preferred that the consensus sequence is Arg-Arg-Arg-Xaa-Ser (SEQ ID NO:1), Arg (or Lys)-Xaa-Arg-Xaa-Xaa-Ser (SEQ ID NO:2), Hyd-Xaa-Arg-Xaa-Xaa-Ser (SEQ ID NO:3) or Xaa-pSer-Xaa-Xaa-Ser (SEQ ID NO:5). In each case the consensus sequence is positioned so that the C-terminal serine of the consensus sequence (which is the serine which is phosphorylated by the protein kinase recognising the consensus sequence) is the serine of the phosphorylatable portion. In a further preferred embodiment the phosphorylatable portion has the amino acid sequence LSFAEPG (SEQ ID NO:2) sequence (which includes sequences with no, one, two, three, four or five residues (other than the serine) conservatively substituted). Thus, the leucine residue immediately N-terminal of the phosphorylatable serine residue corresponds to the "Xaa" residue immediately N-terminal of the serine residue in each of the consensus sequences indicated above. In particularly preferred embodiments, the protein kinase substrate polypeptides are polypeptides of the invention, as discussed further below.

By "conservative substitutions" is intended combinations such as Gly, Ala; Val, Ile, Leu; Asp, Glu; Asn, Gln; Ser, Thr; Lys, Arg; and Phe, Tyr. It is preferred that there are no residues conservatively substituted in the given sequence, though in decreasing order of preference one, two, three, four or five residues may be conservatively substituted).

The common phosphorylatable portion must be antigenic and contain a residue that can be phosphorylated. It is preferred that the Km of the protein kinase for the substrate peptide is less than 1 mM, still more preferably less than (in ascending order of preference) 800, 600, 500, 400, 300, 200 or 100 µM. It is preferred that the Km of the protein kinase for the substrate peptide is no more than (in decending order of preference) 2, 5, 10, 20 or 30 times the Km of the protein kinase for the substrate normally used in assaying that protein kinase (for example as discussed in Example 1). It is preferred that the $V_{max}$ of the protein kinase for the substrate peptide is at least 20, 30, 40, 50, 60, 70, 80, 90 or 100% of the $V_{max}$ of the protein kinase for the substrate normally used in assaying that protein kinase (for example as discussed in Example 1). It will be appreciated that it is a combination of Km and Vmax that is important. The substrate peptide should be phosphorylated in a reasonable time e.g an assay taking hours to complete would not be particularly useful. An assay that preferably takes less than 30 minutes but more preferably 15, 10 or 5 min (or less) would be preferred. It is also important that the assay is robust and does not require excessive amounts of enzyme substrate and antibody due to the cost implications.

The kit of parts may further comprise the specific binding partner, for example antibody preparation, which may be a polyclonal or monoclonal antibody preparation. Methods for preparing suitable antibody preparations will be known to those skilled in the art, and suitable methods are described Examples 1 and 2.

It is preferred that the specific binding partner, for example antibody preparation, is capable of recognising <10 ng of the phosphorylated (or alternatively the unphosphorylated) substrate polypeptide (for example when conjugated to a carrier polypeptide as described in Example 1) when used at 2 µg/ml (for immunoblotting) or 10-20 µg/ml (in modified ELISA format), as described in Example 1. The specific binding partner may preferably have a binding constant ($K_d$) for the phosphorylated (or alternatively the unphosphorylated) substrate polypeptide (or the shared phosphorylatable portion or epitope thereof) of between about $10^{-4}$ and $10^{-16}$ M, preferably between about $10^{-6}$ and $10^{-10}$.

By "binding in a phosphorylation state-sensitive manner" is included the meaning that the specific binding partner is capable of binding to the substrate polypeptide (or the shared epitope, as discussed above) when phosphorylated on the phosphorylatable portion, but is not capable of binding to the substrate polypeptide (or the shared epitope) when it is not phosphorylated on the phosphorylatable portion. Thus, it is preferred that the specific binding partner has at least a 5-fold, preferably 10, 20, 50, 100, 200, 500,1000, 2000 or 5000-fold difference in affinity for the phosphorylated and non-phosphorylated substrate polypeptide. In practice, a specific binding partner prepared and purified/selected using the methods described in Examples 1 and 2 (for example affinity purified using a phosphorylated peptide affinity column and a non-phosphorylated peptide affinity column) is expected to have the required affinity and specificity of binding.

The specific binding partner may be or comprise an entire antibody (usually, for convenience and specificity, a monoclonal antibody, but may also be a polyclonal antibody preparation), a part or parts thereof (for example an $F_{ab}$ fragment or $F(ab')_2$) or a synthetic antibody or part thereof. A specific binding partner comprising only part of an antibody (for example as discussed below) may be advantageous by virtue of more rapid binding kinetics/equilibration or improved solubility. Effector functions of whole antibodies, such as complement binding, are removed. Fab, Fv, ScFv and dAb antibody fragments can all be expressed in and secreted from *E. coli*, thus allowing the facile production of large amounts of the said fragments.

Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies: techniques and Applications", JGR Hurrell (CRC Press, 1982). Bispecific antibodies may be prepared by cell fusion, by reassociation of monovalent fragments or by chemical cross-linking of whole antibodies. Methods for preparing bispecific antibodies are disclosed in Corvalen et al, (1987) *Cancer Immunol. Immunother.* 24, 127-132 and 133-137 and 138-143.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

By "ScFv molecules" is meant molecules wherein the $V_H$ and $V_L$ partner domains are linked via a flexible oligopeptide.

Whole antibodies, and $F(ab')_2$ fragments are "bivalent". By "bivalent" is meant that the said antibodies and $F(ab')_2$ fragments have two antigen combining sites. In contrast, Fab, Fv, ScFv and dAb fragments are monovalent, having only one antigen combining sites. Fragmentation of intact immunoglobulins to produce $F(ab')_2$ fragments is disclosed by Harwood et al (1985) *Eur. J. Cancer Clin. Oncol.* 21, 1515-1522.

IgG class antibodies are preferred.

A further aspect of the invention provides an antibody specific for the epitope formed by the amino acid sequence LSFAEPG (ie with the serine unphosphorylated) (SEQ ID NO:6). A further aspect of the invention provides an antibody specific for the epitope formed by the amino acid sequence LpSFAEPG (ie with the serine phosphorylated) (SEQ ID NO:7).

By "specific" is included the meaning that the antibody binds to the epitope formed by the amino acid sequence LSFAEPG (SEQ ID NO:6)but not to the epitope formed by the amino acid sequence LpSFAEPG (SEQ ID NO:7)or vice versa.

By the term "antibody" is included synthetic antibodies and fragments and variants (for example as discussed above) of whole antibodies which retain the antigen binding site.

A further aspect of the invention provides a polypeptide of less than 40, 30, 20, 19, 18, 17, 16, 15, or 14 amino acids in length wherein the polypeptide is not a fragment of glycogen synthase kinase 3, and wherein the polypeptide comprises the amino acid sequence LSFAEPG (SEQ ID NO:6) (which includes sequences with no, one, two, three, four or five residues (other than the serine) conservatively substituted) and further comprising a specificity conferring portion comprising an amino acid sequence (which may overlap with the sequence LSFAEPG (SEQ ID NO:6)) corresponding to a consensus sequence for a protein kinase, wherein the sequence corresponding to the consensus sequence is positioned relative to the sequence LSFAEPG (SEQ ID NO:6) such that the protein kinase is capable of phosphorylating the polypeptide at the serine residue of the sequence LSFAEPG (SEQ ID NO:6). It is particularly preferred that the substrate polypeptide is 13, 12, 11, 10 or 9 amino acids in length. It is preferred that the amino acid sequence corresponding to the consensus sequence extends to the N-terminus of the sequence LSPAEPG (SEQ ID NO:6).

In particularly preferred embodiments, the consensus sequence is Arg/Lys-Arg/Lys-Arg/Lys-Xaa-Ser (SEQ ID NO:8), Arg/Lys-Xaa-Arg/Lys-Xaa-Xaa-Ser (SEQ ID NO:9), Hyd-Xaa-Arg-Xaa-Xaa-Ser (SEQ ID NO:3) or Xaa-pSer-Xaa-Xaa-Ser (SEQ ID NO:5). In each case the consensus sequence is positioned so that the C-terminal serine of the consensus sequence (which is the serine which is phosphorylated by the protein kinase recognising the consensus sequence) is the serine of the LSFAEPG sequence (SEQ ID NO:6).

Arginines other than the Arg in Hyd-Xaa-Arg-Xaa-Xaa-Ser (SEQ ID NO:3) may be replaced with Lysine.

Thus, it is preferred that the polypeptide has or comprises the amino acid sequence Arg-Arg-Arg-Leu-Ser-Phe-Ala-Glu-Pro-Gly (SEQ ID NO:4), Arg-Xaa-Arg-Xaa-Leu-Ser-Phe-Ala-Glu-Pro-Gly (SEQ ID NO: 29), Hyd-Xaa-Arg-Xaa-Leu-Ser-Phe-Ala-Glu-Pro-Gly (SEQ ID NO:30) or Xaa-pSer-Xaa-Leu-Ser-Phe-Ala-Glu-Pro-Gly (SEQ ID NO:12).

In particularly preferred embodiments, the polypeptide has the amino acid sequence Arg-Arg-Arg-Leu-Ser-Phe-Ala-Glu-Pro-Gly (SEQ ID NO:4), Arg-Ala-Arg-Thr-Leu-Ser-Phe-Ala-Glu-Pro-Gly(SEQ ID NO:16) or Lys-Lys-Leu-Asn-Arg-Thr-Leu-Ser-Phe-Ala-Glu-Pro-Gly (SEQ ID NO:13).

A further aspect of the invention provides a polypeptide of the preceding aspect of the invention in which the serine in the sequence LSFAEPG is(SEQ ID NO:6) is replaced by phosphoserine(SEQ ID NO:7).

The three-letter and one-letter amino acid code of the IUPAC-IUB Biochemical Nomenclature Commission is used herein. The sequence of polypeptides are given N-terminal to C-terminal as is conventional. In particular, Xaa represents any amino acid. It is preferred that the amino acids are L-amino acids, in particular it is strongly preferred that the SIM, for example a PP(T/N)K motif, consists of L-amino acid residues. It is preferred that the amino acid residues immediately flanking (such as those within 10 to 20 residues) of the SIM, for example flanking the PP(T/N)K motif are L-amino acids residues, but they may be D-amino acid residues.

The polypeptides may be made by methods well known in the art and as described below and in Example 1, for example using molecular biology methods or automated chemical peptide synthesis methods.

Peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzene-sulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclo-hexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

Alternatively, polypeptides may be synthesised by expression of recombinant nucleic acid, as well known to those skilled in the art. Methods well known to those skilled in the art can be used to construct expression vectors containing the coding sequence and, for example appropriate transcriptional or translational controls.

A desirable way to modify the DNA encoding the polypeptide of the invention is to use the polymerase chain reaction as disclosed by Saiki et al (1988) *Science* 239, 487-491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

The nucleic acid encoding the desired polypeptide is then expressed in a suitable host to produce the desired polypeptide. Thus, the DNA encoding the polypeptide may be used in accordance with known techniques, appropriately modified in view of the teachings contained herein, to construct an expression vector, which is then used to transform an appropriate host cell for the expression and production of the polypeptide. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Many expression systems are known, including systems employing: bacteria (eg. *E.coli* and *Bacillus subtilis*) transformed with, for example, recombinant bacteriophage, plasmid or cosmid DNA expression vectors; yeasts (eg. *Saccaro-*

*myces cerevisiae*) transformed with, for example, yeast expression vectors; insect cell systems transformed with, for example, viral expression vectors (eg. baculovirus) ; plant cell systems transfected with, for example viral or bacterial expression vectors; animal cell systems transfected with, for example, adenovirus expression vectors.

It will be appreciated that peptidomimetic compounds may also be useful. Thus, by "polypeptide" or "peptide" we include not only molecules in which amino acid residues are joined by peptide (—CO—NH—) linkages but also molecules in which the peptide bond is reversed. Such retro-inverso peptidomimetics may be made using methods known in the art, for example such as those described in Mézière et al (1997) *J. Immunol.* 159, 3230-3237, incorporated herein by reference. This approach involves making pseudopeptides containing changes involving the backbone, and not the orientation of side chains. Mézière et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the Ca atoms of the amino acid residues is used; it is particularly preferred if the linker moiety has substantially the same charge distribution and substantially the same planarity as a peptide bond.

It will be appreciated that the peptide may conveniently be blocked at its N- or C-terminus so as to help reduce susceptibility to exoproteolytic digestion.

Thus, it will be appreciated that the substrate polypeptide, for example which comprises the amino acid sequence LSFAEPG (SEQ ID NO:6) may be a peptidomimetic compound, as described above, though this is not preferred.

A further aspect of the invention comprises the use of a polypeptide of the invention or a phosphorylated polypeptide of the invention in an assay of protein kinase or phosphatase activity. A further aspect of the invention comprises the use of an antibody of the invention in an assay of protein kinase or phosphatase activity.

A further aspect of the invention provides a method for screening for protein kinases in a sample which may contain protein kinases comprising exposing a polypeptide or phosphorylated polypeptide of the invention or polypeptides of a kit of the invention to the sample and determining whether and optionally to what extent the said polypeptide or polypeptides are phosphorylated.

The sample may be a cellular extract or a fraction of a cellular extract. For example, the polypeptides may be used for monitoring kinase or phosphatase activity during a purification protocol.

A further aspect of the invention provides a method for assessing the activity of a protein kinase, comprising the steps of exposing the protein kinase to a polypeptide of the invention, and determining whether and optionally to what extent the said polypeptide is phosphorylated.

A further aspect of the invention provides a method for assessing the activity of a first protein kinase and a second protein kinase, comprising the steps of exposing the first protein kinase to a first polypeptide of a kit of the first aspect of the invention, and exposing the second protein kinase to a second polypeptide of a kit of the first aspect of the invention; and determining whether and optionally to what extent the said polypeptide is phosphorylated. In a particularly preferred embodiment, the polypeptide of the kit are polypeptides of the invention, as discussed above, ie comprise the amino acid sequence LSFAEPG(SEQ ID NO:6).

The methods may be used in measuring or characterising the substrate specificity of the protein kinases. In characterising substrate specificity, the protein kinase may be exposed to more than one polypeptide of the invention, or more than one substrate polypeptide of a kit of the invention (ie more than one substrate polypeptide with the same phosphorylatable (or phosphorylated) portion).

Thus, a further aspect of the invention provides a method for characterising the substrate specificity of a protein kinase, comprising the steps of exposing the protein kinase to a first polypeptide of a kit of the first aspect of the invention, and exposing the protein kinase to a second polypeptide of a kit of the first aspect of the invention; and determining whether and optionally to what extent the said polypeptides are phosphorylated. In a particularly preferred embodiment, the specified polypeptides of the kit are unphosphorylated polypeptides of the invention, ie comprising the amino acid sequence LSFAEPG(SEQ ID NO:6).

This may be useful in selecting a substrate polypeptide for measuring the activity of the protein kinase Alternatively, a substrate polypeptide may be selected for a particular protein kinase on the basis of the consensus sequence for the protein kinase. This may be confirmed by comparing the activity of the protein kinase with the selected substrate with the activity with one or more other substrates.

The methods of the invention may be used for measuring the activity of the protein kinase for example in the presence of a test compound. Thus, the methods may further comprise the step of exposing the protein kinase to a test compound, and measuring the protein kinase activity in the presence and absence of the test compound. Compounds which affect the activity of the protein kinase (which may include affecting the substrate specificity) may be selected.

The agents identified or obtained according to the above aspects of the is invention (as well as the screening methods provided by farther aspects of the invention, as discussed below) may be a drug-like compound or lead compound for the development of a drug-like compound. Thus, the methods may be methods for identifying a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons and which may be water-soluble. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise, too toxic or has poor bioavailability) may provide a starting-point for the design of other compounds that may have more desirable characteristics.

The compounds identified in the methods of the invention may themselves be useful as a drug or they may represent lead compounds for the design and synthesis of more efficacious compounds.

It will be understood that it will be desirable to identify compounds that may modulate the activity of the protein kinase or phosphatase in vivo. Thus it will be understood that reagents and conditions used in the method may be chosen such that the interactions between the said protein kinase or phosphatase and its substrate are substantially the same as in vivo.

Preferred protein kinases for assay by the methods of the invention (particularly when using a polypeptide comprising the epitope LSFAEPG (SEQ ID NO: 6)) include protein kinases that do not have a strong sequence preference C-terminal of the phosphorylated residue, for example members of the PKA family (including, for example, isoforms of PKG, ROCKII and PKC), PKB family (including, for example, isoforms of PKB, SGK, MSK, MAPKAP-K1 and S6K) or MAPKAP-K2 family (including, for example, MAPKAP-K3, PRAK, CHK1, CHK2, AMPK and CaMKII) or CK1 isoforms and subfamily.

In one embodiment, the compound decreases the activity of said protein kinase For example, the compound may bind substantially reversibly or substantially irreversibly to the active site of said protein kinase. In a further example, the compound may bind to a portion of said protein kinase that is not the active site so as to interfere with the binding of the said protein kinase to its substrate. In a still further example, the compound may bind to a portion of said protein kinase so as to decrease said protein kinase's activity by an allosteric effect. This allosteric effect may be an allosteric effect that is involved in the natural regulation of the said protein kinase's activity, for example in the activation of the said protein kinase by an "upstream activator".

In a further embodiment, the compound increases the activity of said protein kinase. For example, the compound may bind to a portion of said protein kinase that is not the active site so as to aid the binding of the said protein kinase to its substrate. In a still further example, the compound may bind to a portion of said protein kinase so as to increase said protein kinase activity by an allosteric effect. This allosteric effect may be an allosteric effect that is involved in the natural regulation of the said protein kinase activity for example in the activation of the said protein kinase by an "upstream activator".

The common substrates may also be useful in binding assays, for example in which the effect of a compound on the binding of the substrate to a protein kinase is measured.

Phosphorylation of the substrate polypeptides may be assessed by methods involving radioactivity, as well known to those skilled in the art, for example as summarised above and as used in Example 1. However, it is preferred that non-radioactive methods are used. In particular, the phosphorylation-state specific interaction between the substrate polypeptides and the specific binding partner may be used in detecting and optionally quantifying the phosphorylation of the substrate polypeptides, preferably in a non-radioactive method. Suitable techniques will be known to those skilled in the art in relation to tyrosine-phosphorylated substrates (using anti-phosphotyrosine antibodies) and may be adapted for use in relation to the present invention. It is preferred that a fluorescence-based (or less preferably radioactive) method is used.

For example, the interaction may be measured by any method of detecting/measuring a protein/protein interaction, as discussed further below. Suitable methods include ELISA methods and fluourescence energy resonance transfer (FRET) methods, well known to those skilled in the art, in which binding of two fluorescent labelled entities may be measured by measuring the interaction of the fluorescent labels when in close proximity to each other. Surface plasmon resonance methods may also be used. Techniques described in GB Application Nos 0018908.4 and 0021685.3 (supra), adapted in view of the present teaching, may also be useful. Fluorescence polarisation (FP) and fluorescence correlation spectroscopy (FCS) may also be used.

Conjugates of the substrate peptide and/or binding partner (for example antibody) may be useful, for example fluorescent, iodinated or biotin labelled conjugates.

It will be appreciated that screening assays which are capable of high throughput operation will be particularly preferred. An SPA-based (Scintillation Proximity Assay; Amersham International) system may be used, as well know to those skilled in the art, though non-radioactive methods are preferred. For example, the substrate polypeptide may be immobilised on the SPA beads.

It will be appreciated that the screening assays of the invention are useful for identifying compounds which may be useful in the treatment of (for example) diabetes, defects of glycogen metabolism, cancer (including melanoma), inflammatory conditions, ischaemic conditions, for example stroke, thrombosis or tendency to thrombosis (for example useful as an antithrombotic agent).

The "drug-like compounds" and "lead compounds" identified in the screening assays of the invention are suitably screened in further screens to determine their potential usefulness in treating diabetes, defects of glycogen metabolism, cancer (including melanoma), inflammatory conditions, ischaemic conditions, for example stroke, or thrombosis or tendency to thrombosis. Additional screens which may be carried out include determining the effect of the compounds on blood glucose levels, tumour growth or blood clotting tendency/time, as appropriate. This may typically be done in rodents.

A further aspect of the invention provides the use of a compound identified using a method of the invention for modulating the activity of a protein kinase or phosphatase. It is preferred that the compound is not previously known as a modulator of protein kinase activity.

The invention will now be described in more detail by reference to the following, non-limiting Figures and Examples.

Any published documents referred to herein are hereby incorporated by reference.

FIGURE LEGENDS

FIG. 1. Generation of a phospho-specific antibody that recognises the epitope LpSFAEPG(SEQ ID NO:7).

Aliquots (10 ng or 100 ng) of the peptide LpSFAEPGC (SEQ ID NO: 17) conjugated to bovine serum albumin were spotted on to a nitrocellulose membrane and immunoblotted with the phospho-specific antibody raised against the phospho-peptide immunogen in the presence or absence of the peptides shown on the right. The prefix "p" before S denotes the serine-phosphorylated form of the peptide.

Figure 2:
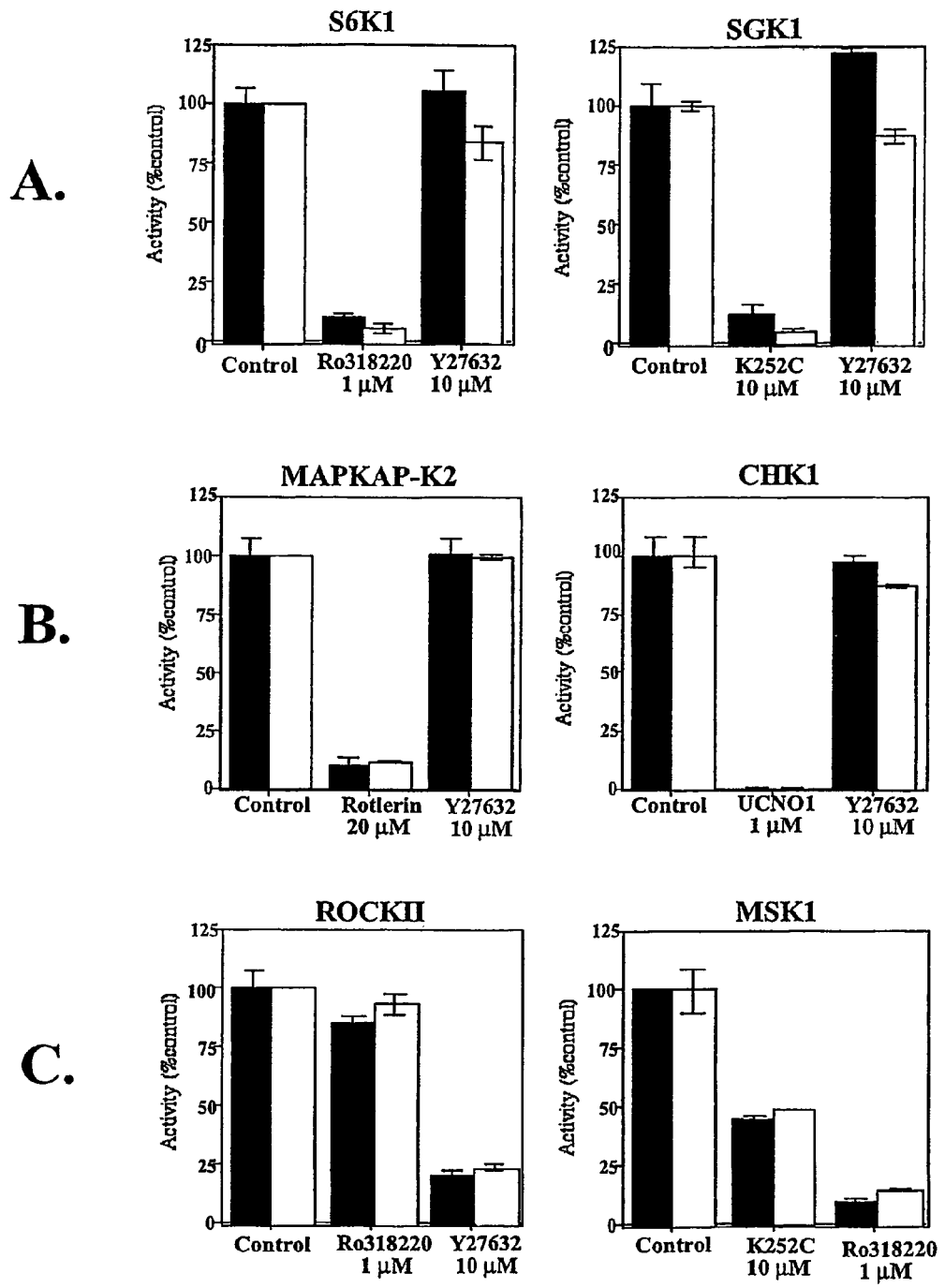

FIG. 2. Comparison of the new ELISA based protein kinase-based assay with the standard radioactive filter-binding assay.

The protein kinases indicated were assayed by the ELISA-method (open bars) or standard radioactive assay (filled bars) using the peptide substrates RARTLSFAEPG (SEQ ID NO:16) (A), KKLNRTLSFAEPG (SEQ ID NO:13) (B) and RRRLSFAEPG (SEQ ID NO:4) (C) and in the presence or absence of the kinase inhibitors shown. The results are shown relative to control incubations in the absence of inhibitors and are presented as standard error of the mean for four determi-

EXAMPLE 1

A Non-Radioactive Method for the Assay of Many Serine/Threonine Specific Protein Kinases Materials and Methods Chemicals and Peptides Ro 318220, K252c and Rottlerin were purchased from Calbiochem-Novabiochem Corp. (La Jolla, Calif., U.S.A). Y27632 was obtained by chemical synthesis, while UCN01 was a gift from Dr Carl Smythe, School of Life Sciences, University of Dundee. Histone H1 was purchased from Life Technologies (Paisley, Scotland, UK). All peptides were synthesised by Dr Graham Bloomberg (Department of Biochemistry, University of Bristol, U.K.) or by Mr F. B. Caudwell in this Unit.

Peptides may be synthesised on either a Perseptive Biosystems 9050 or an Applied Biosystems Pioneer (see, for example, Askin et al (1998) *Biochlemistry* 37, 11670-11678.

Processing and quality control. After synthesis the peptide resin is washed with methanol and dichloromethane and dried under vacuum for a minimum of 3 hours. Peptides are cleaved from the resin with cocktails of TFA (trifluoroacetic acid) containing appropriate scavengers. These are selected according to sequence and may contain water, phenol, ethanedithiol, thioanisole and triisobutylsilane, usually in a ratio of 90:10 where 90 is the % TFA. A proportion of the TFA is then evaporated and peptides are precipitated with diethyl ether, washed, pelleted, dried and then freeze-dried. Purification is performed using reversed phase HPLC when necessary. C18 columns are eluted with gradients of water/acetonitrile containing 0.1% TFA. The mass of the purified peptide is determined using electrospray mass spectrometry, performed using a Micromass Quattro.

Source and Purification of Protein Kinases (See [4] for Further Details)

Apart from the AMP-activated protein kinase (AMPK, a gift from Drs S. Hawley and D. G. Hardie), cGMP-dependent protein kinase (PKG, a generous gift from Drs Susan Lohmann and Ulrich Walter, University of Wurzburg, Germany) and the catalytic subunit of cyclic AMP-dependent protein kinase (PKA, a gift from Dr C. Smythe), which were isolated from rat liver, bovine lung and bovine heart, respectively, all other protein kinases were expressed as either GST-fusion or His-tagged proteins (by Ms C. Clark, Ms F. Douglas, Dr A. Paterson or Ms G. Wiggin, in this Division). The expressed proteins all corresponded to the human sequences apart from the rat Rho-dependent protein kinase (ROCK-II) and rat mitogen-activated protein kinase (MAPK) activated kinase-1a (MAPKAP-K1a, also called RSK). GST-fusion proteins were purified on GSH-agarose (Amersham Pharmacia Biotech, Amersham, UK) and His-tagged proteins on Ni-NTA agarose (Qiagen) essentially according to the manufacturer's instructions. All the protein kinases used in this study are available from Upstate Biotechnology Inc. (Lake Placid, N.Y., USA), apart from the α-isoform of calmodulin-dependent protein kinase II (CaMKII), MAPKAP-K3 and PKG.

Protein Linases Expressed in *E.coli*

The following enzymes were expressed in *E.coli* as GST-fusion proteins: extracellular signal-regulated protein kinase-2 (ERK2), stress-activated protein kinase-2a (SAPK2a, also called p38). MAPKAP-K2, MAPKAP-K3, CaMKII (Calbiochem-Novabiochem Corp.) and Checkpoint Kinase 2 (CHK2). CHK2 contained an additional His-tag at the extreme C-terminus, to aid purification of the full-length product. ERK2 was activated using Raf-activated MAPK kinase 1 (MKK1) and SAPK2a/p38 using a constitutively active mutant of MKK6. MKK1 and MKK6 were also expressed in *E.coli* as GST-fusion proteins.

Protein Linases Expressed in Sf21 Cells.

The following enzymes were expressed in Sf21 cells: Checkpoint Kinase 1 (CHK1), p38 regulated/activated kinase (PRAK), protein kinase Bα (PKBα), MAPKAP-K1a and serum and glucocorticoid-induced kinase 1 (SGK1[S422D] and lacking the N-terminal 59 residues), mitogen and stress-activated protein kinase 1 (MSK1), p70 ribosomal S6 kinase 1 (S6K1[T412E], lacking the C-terminal 104 residues), c-Raf, protein kinase C (PKCα, Calbiochem Novachem Corp.), rat ROCKII[1-543].

Activation of Protein Kinases

MAPKAP-K2 and MAPKAP-K3 were activated with incubation with MgATP and extracellular signal regulated protein kinase-2 (ERK2); ERK2 with MAPK kinase-1 (MKK1); MKK1 with Raf; SAPK2a/p38 with MKK6; PRAK with SAPK2a/p38; PKBA, SGK1 and S6K1 with PDK1.

Antibodies

Antibodies that recognise the common seven residue phosphorylated motif (LpSFAEPG) (SEQ ID NO:7) contained within each of the three generic peptide substrates described under results, were raised against the peptide LpSFAEPGC (SEQ ID NO:17) (where pS represents phosphoserine). The C-terminal cysteine residue was added to enable coupling to keyhole limpet haemocyanin. The peptide-protein conjugate was injected into sheep at Diagnostic Scotland (Carluke, U.K.) and the anti-sera purified on protein G-Sepharose (Amersham Pharmacia Biotech) by Dr J. Leitch in this Unit. Antibodies were used at a concentration of 2 µg/ml for immunoblotting and 10-20 µg/ml for detection of phosphorylated peptides in the modified ELISA format. Rabbit anti-sheep antibodies conjugated to peroxidase were obtained from Pierce (Tattenhall, Cheshire, UK) and used at 1/10,000 dilution.

Kinase Assays

All protein kinase assays were linear with respect to time. The assays with standard peptide substrates have been described previously [4]. The assays with the three generic peptides introduced in this example were carried out in the same buffers as follow. Unlabelled or biotinylated substrate peptides were assayed for 10 min at 30° C. in 50 µl incubations, in the presence of 0.1 mM [$\gamma^{32}$P]ATP or unlabelled ATP. Radioactive assays were terminated by spotting 40 µl of each incubation on to phosphocellulose paper followed by immersion in 75 mM phosphoric acid. All papers were subsequently washed a further three times in phosphoric acid, once in acetone, then dried and counted for radioactivity. Non-radioactive assays were terminated by the addition of EDTA to a final concentration of 20 mM, then diluted with an equal volume of phosphate-buffered saline (PBS), containing 0.1% Tween 20 and the biotinylated peptides captured by incubation for 60 min on pre-washed, 96 well Streptavidin coated plates (Equilon A/S, Vedbaek, Denmark). The plates were washed six times (five min per wash) in PBS, 0.1% Tween 20 and then incubated for 60 min with antibody (10-20 µg/ml) raised against the generic phospho-specific antibody (see above). The plates were then washed six times (five min per wash) in PBS, 0.1% Tween 20 and binding of the phospho-specific antibody detected by incubating the plates with peroxidase-conjugated anti-sheep antibodies (Pierce). The plates were washed a further six times as above and binding visualised using enhanced chemiluminescence (Amersham Pharmacia Biotech) on a FujiFilm LAS-1000 CCD camera. Signals were quantitated on LAS-1000IR software (FujiFilm).

Results and Discussion.

The Development of Generic Peptide Substrates

As noted above, many protein kinases phosphorylate serine residues that lie in particular amino acid motifs. We tested a number of peptides that share a common C-terminal epitope that might be used to generate a single phospho-specific antibody capable of assaying many protein kinases. These studies resulted in the development of the three generic peptides shown in Table 1, that contain a common seven residue epitope related to the sequence surrounding the serine in glycogen synthase kinase 3 that is phosphorylated by PKB [9]. Using the standard radioactive filter-binding assay, one or more of these three peptides was phosphorylated efficiently by the 16 different protein kinases that we tested, which fall into several different kinase subfamilies. Indeed, in many cases, one of these three peptides proved to be phosphorylated as efficiently, and sometimes even more efficiently, than the substrates in routine use for their assay.

Table 1. Kinetic Parameters for Peptide Phosphorylation by a Number of Protein Kinases.

PKBα, SGK1, MSK1, S6K1, PKA, PKG, ROCKII, MAPKAP-K2, MAPKAP-K3, PRAK, CHK1 and CHK2 were assayed in 50 mM Tris/HCl pH 7.5, 0.1 mM EGTA, 0.1% (v/v) β-mercaptoethanol, 0.01% (w/v) Brij-35, the AMPK in 50 mM Hepes pH 7.4, 1 Mm dithiothreitol, 0.02% Brij-35 and 0.2 mM AMP, PKCα in 20 mM Hepes, pH 7.4, 0.03% Triton X-100, 0.1 mM CaCl$_2$, 0.1 mg/ml phosphatidylserine and 10 μg/ml 1,2-dioleoyl-sn-glycerol and CaMKII in 50 mM Hepes, pH 7.4, 5 mM CaCl$_2$, 0.03 mg/ml calmodulin. The $V_{max}$ values for the three generic peptides developed in this example are given relative to the standard peptide substrates for each protein kinase. The standard peptide substrates (single amino acid code) were:—GRPRTSSFAEG (SEQ ID NO:18) (PKBα, SGK1),LRRASLG (SEQ ID NO:19) (MSK1, S6K1, PKA), KEAKEKRQEQIAKRRRLSSLRASTSKSGGSQK (SEQ ID NO:20) (ROCK-II and PKG), KKLNRTLSVA (SEQ ID NO:21) (MAPKAP-K2 and MAPKAP-K3), KKLRRTLSVA (SEQ ID NO:22) (PRAK); KKKVSRSGLYRSPSMPENLNRPR (SEQ ID NO:23) (CHK1 and CHK2) HMRSAMSGLHLVKRR (SEQ ID NO:24) (AMPK), MHRQETVDCLK (SEQ ID NO:25) (CaM-KII), histone H1 (PKC).

TABLE 1

A.

| | RARTLSFAEPG (SEQ ID NO:16) | | Standard Substrate | |
|---|---|---|---|---|
| Enzyme | Km (μM) | Relative Vmax (%) | Km (μM) | Relative Vmax (%) |
| MAPKAP-K2 | 5 | 52 | 7 | 100 |
| MAPKAP-K3 | 30 | 105 | 18 | 100 |
| PRAK | 40 | 40 | >100 | 100 |
| CHK1 | 5 | 117 | 5 | 100 |
| CHK2 | >300 | 221 | >300 | 100 |
| AMPK | 75 | 114 | 80 | 100 |
| CaMKII | 300 | 80 | 60 | 100 |

TABLE 1-continued

B.

| | KKLNRTLSFAEPG (SEQ ID NO:13) | | Standard Substrate | |
|---|---|---|---|---|
| Enzyme | Km (μM) | Relative Vmax (%) | Km (μM) | Relative Vmax (%) |
| PKBα | 2 | 100 | 4 | 100 |
| SGK1 | 4 | 105 | 4 | 100 |
| MSK1 | 2 | 156 | 6 | 100 |
| S6K1 | 6 | 124 | 8 | 100 |

C.

| | RRRLSFAEPG (SEQ ID No 4) | | Standard Substrate | |
|---|---|---|---|---|
| Enzyme | Km (μM) | Relative Vmax (%) | Km (μM) | Relative Vmax (%) |
| PKA | 30 | 161 | 18 | 100 |
| PKG | 50 | 122 | 5 | 100 |
| ROCKII | >100 | 39 | 5 | 100 |
| PKCα | >500 | 39 | 2 | 100 |

Although PKC could be assayed perfectly well using the peptide Arg-Arg-Arg-Leu-Ser-Phe-Ala-Glu-Pro Gly (SEQ ID NO:4) (Table 1), this substrate was inferior to other substrates that have been used to assay this protein kinase. This is because PKC prefers basic residues C-terminal to the site of phosphorylation, which are not present in the epitope, in addition basic residues N-terminal to the site of phosphorylation [5].

Generation of a Phospho-specific Antibody to the common C-terminal Epitope.

The major purpose of the present study was to simplify "high throughput screening" of protein kinases by developing a non-radioactive assay applicable to the assay of many protein kinases. In order to do this, we therefore generated a phospho-specific antibody capable of recognising the phosphorylated epitope (LpSFAEPG) (SEQ ID NO:7)common to the three generic substrates (see Methods). This antibody recognised <10 ng of the conjugated phosphopeptide antigen (FIG. 1). The ability of the antibody to recognize the three generic substrate peptides in their phosphorylated form was established by competition studies. These experiments showed that the phosphopeptide antibody was not only neutralised by pre-incubation with the seven residue phosphopeptide antigen, but also by each of the phosphorylated generic peptide substrates. In contrast, the unphosphorylated forms of the same peptides were unable to neutralise the antibody (FIG. 1).

Development of a Non-Radioactive Assay for Many Protein Kinases

We then used the three generic peptides, in conjunction with the phospho-specific antibody described above, to set up a simple non-radioactive ELISA based assay for subset of the protein kinase in Table 1 (see Methods). The assays were run in parallel with standard radioactive filter-binding assays under linear rate conditions where less than 10% of the peptide was phosphorylated (FIG. 2). The results showed that the non-radioactive assay was of similar accuracy to the standard radioactive procedure and a similar degree of inhibition was observed in both assays in the presence of known inhibitors of these protein kinases [5].

Concluding Remarks.

In this example we have described a simple non-radioactive assay that is suitable for the high throughput screening of many protein kinases. We consider that the same three peptides can be used as substrates by all the closely related isoforms the protein kinases studied, and probably by most, if not all, of the other members of the same kinase subfamilies. We also consider that additional peptides with the same C-terminal epitope may be used to assay other protein kinases that recognise a specific motif N-terminal to the site of phosphorylation. For example, CK1 (previous called casein kinase1) phosphorylates serine residues that lie three residues C-terminal to another phosphoserine residue [10]. It may therefore phosphorylate peptides of the type Xaa-pSer-Xaa-Leu-Ser-Phe-Ala-Glu-Pro-Gly (SEQ ID NO:12). We therefore consider that our strategy is applicable to at least 50 and probably more than 100 protein kinases. The assay we have developed is not applicable to protein kinases that have a stringent requirement for a particular motif or residue C-terminal to the site of phosphorylation. For example, MAP kinases and cyclin-dependent protein kinases have an absolute requirement for a proline residue immediately C-terminal to the site of phosphorylation [5], which is a negative determinant for the protein kinases tested in this example. Similarly CK2 requires several consecutive acidic residues C-terminal to the site of phosphorylation, while the DNA-dependent protein kinase requires a C-terminal glutamine [5]. However, in view of the results presented herein, a second series of peptide substrates with a common N-terminal epitope may be useful in assaying many protein kinases that require a specific C-terminal motif for phosphorylation.

EXAMPLE 2

Preparation of Monoclonal Phospho-Specific Antibody

The peptide may be coupled to a carrier protein, for example Keyhole limpet Haemocyanin (KLH). The carrier protein (for example KLH) is dissolved to a concentration of about 10 mg/ml in PBS. A solution of m-maleimidobenzoyl-N-hydroxysuccinimide ester (MBS) in dimethylformamide is prepared. 0.1 volume of MBS is added dropwise to the carrier protein solution, vortexing to avoid a high local concentration. 1 ml of a 10 mg/ml solution of the peptide is added. The activated carrier and uncoupled peptide are separated using a P10 column in PBS.

Monoclonal antibodies are generated using methods as described in Harlow & Lane (1988) Antibodies: A Laboratory Manual. Cold Spring Harbor Laboratory. ISBN 0-87969-314-2. Following production of hybridomas, the produced IgG is purified from the medium supernatant by chromatography on a Protein A-immobilised matrix. The phosphospecific antibodies are then immuno-affinity purified using a protocol as follows.

Prepare an affinity column with the phosphorylated peptide using standard procedures. Also prepare an affinity column with the dephosphorylated peptide using standard procedures. Wash the prepared "phospho" column with 2 column volumes of 1× TSB/Tween 20 0.1%. Dilute the antibody serum (for example 40 ml) 3-fold in 1× TBS/Tween 20 0.1% and filter through 0.2 μm filter. Load the diluted serum through the column twice. Wash the column with 20 mM Tris pH7.5+0.4 M NaCl until $OD_{595\ nm}$ is <0.003 (to remove unbound antibody/protein). Elute with 50 mM Glycine pH2.5 into 1.5 ml eppendorfs containing 200 μl 1.5M Tris pH 8.0; collect 1 ml fractions. Check the protein concentration of the fractions using the Bradford assay; collect the fractions with high protein concentrations (>0.2 mg/ml). Store overnight at 4° C. Remeasure the protein concentration.

Wash the "dephospho" column with 2 column volumes of 1× TBS/Tween 20 0.1%. Load the column with the pooled fractions. Collect the flow-through; this is the antibody specific for the phosphorylated form of the peptide. Measure the protein concentration and store at −20° C. Wash both the "phospho" and "dephospho" columns with two column volumes of 1% SDS. Store the columns in 20% ethanol. Prior to reuse, wash with 10× TBS/Tween 20 1% prior to washing with 1× TBS/Tween 20 0.1%.

REFERENCES

1. Liu, J., Farner, J. D., Lane, W. S., Friedman, J., Weissman, I. And Schreiber S. L. (1991) calcineurin is a common target of cyclophilin-cyclosporin A and FKBP-FK506 complexes. Cell 66, 807-815
2. Brown, E. J., Albers, M. W., Shin, T. B., Ichikawa, K., Keith, C. T., Lane, W. S. and Schreiber, S. L. (1994) A mammalian protein targeted by G1-arresting rapamycin-receptor complex. Nature 369, 756-758.
3. Morin, M. (2000) From oncogene to drug: development of small molecule tyrosine kinase inhibitors as anti-tumor and anti-angiogenic agents. Oncogene 19, 6574-6583.
4. Davies, S., Reddy, H., Caivano, M. and Cohen, P. (2000) Specificity and mechanism of action of some commonly used protein kinase inhibitors. Biochem. J. 351, 95-105
5. Pinna, L. A. and Ruzzene, M. (1996) How do protein kinases recognise their substrates? Biochim. Biophys. Acta 1314, 191-225
6. Leighton, I. A., Dalby, K. N., Caudwell, F. B., Cohen, P. T. W. and Cohen, P. (1995) Comparison of the specificities of p70 S6 kinase and MAPKAP-kinase-1 identifies a relatively specific substrate for p70 S6 kinase: the N-terminal kinase domain of MAPKAP-K1 is essential for peptide phosphorylation. FEBS Lett 375, 289-293.
7. Kobayashi, T. and Cohen, P. (1999) Activation of serum and glucocorticoid-regulated protein kinase by agonists that activate phosphatidylinositide 3-kinase is mediated by 3-phosphoinositide-dependent protein kinase-1 (PDK1) and PDK2. Biochem J. 339, 319-328
8. Stokoe, D., Caudwell, B., Cohen, P. T. W. and Cohen, P. (1993) The substrate specificity and structure of mitogen-activated protein (MAP) kinase-activate protein kinase-2. Biochem. J. 296, 843-849.
9. Cross, D. A. E., Alessi, D. R., Cohen, P., Andjelkovich, M. and Hemmings, B. A. (1995) Inhibition of glycogen synthase kinase-3 by insulin mediated by protein kinase B. Nature 378, 785-789.
10. Flotow, H., Graves, P. R., Wang, A. Q., Fiol C. J., Roeske, R. W. and Roach, P. J. (1990). Phosphate groups as substrate determinants for casein kinase I action. J. Biol. Chem., 265, 14264-14269.

EXAMPLE 3

Compound Screening Method

Using homogeneous FRET analysis the compound of interest could be incubated with biotinylated peptide substrate, enzyme and europium labelled antibody in buffer containing streptavidin APC. Phosphorylation of the peptide would result in the europium labelled antibody binding to the substrate so that the europium is in close proximity to the APC. This allows electron transfer from the europium to the APC which can be measured at an excitation wavelength of 610 nm and emission wavelength of 660 nm.

The invention claimed is:

1. A kit comprising two or more protein kinase substrate polypeptides, each said substrate polypeptide having a sequence comprising a specificity conferring portion and a phosphorylatable portion, wherein the specificity conferring portion is recognized as a substrate by a protein kinase, and the specificity conferring portion is different for each said substrate polypeptide, and, wherein the phosphorylatable portion of each said substrate polypeptide is SEQ ID NO: 6.

2. The kit as defined in claim 1 wherein the phosphorylatable portion of at least one said protein kinase substrate polypeptide is phosphorylated.

3. The kit of claim 1 wherein each said protein kinase substrate polypeptide is of less than 40, 30, 20, 19, 18, 17, 16, 15, or 14 amino acids in length.

4. The kit of claim 3 wherein said protein kinase substrate polypeptide is 13, 12, 11, 10 or 9 amino acids in length.

5. The kit of claim 4 wherein the protein kinase substrate polypeptide is a substrate for a serine/threonine protein kinase.

6. The kit of claim 1 farther comprising a specific binding partner.

7. The kit of claim 6 wherein the specific binding partner is an antibody.

8. An antibody specific for the epitope formed by the amino acid sequence of SEQ ID NO: 6.

9. An antibody specific for the epitope formed by the amino acid sequence LpSFAEPG (SEQ ID NO: 7).

10. A polypeptide of less than 13 amino acids in length wherein the polypeptide is not a fragment of glycogen synthase kinase 3, and wherein the polypeptide comprises a sequence comprising SEQ ID NO: 6 and a specificity conferring portion, wherein the specificity conferring portion comprises an amino acid sequence corresponding to a consensus sequence for a protein kinase, and the sequence corresponding to the consensus sequence is positioned relative to SEQ ID NO: 6 such that the protein kinase phosphorylates the polypeptide at the serine residue of SEQ ID NO:6, and said consensus sequence is SEQ ID NO: 8, SEQ ID NO: 9, SEQ ID: NO:2, or SEQ ID NO:5.

11. The polypeptide of claim 10 wherein the polypeptide is 13, 12, 11, 10, or 9 amino acids in length.

12. The polypeptide of claim 10 wherein the amino acid sequence corresponding to the consensus sequence extends to the N-terminus of SEQ ID NO: 6.

13. The polypeptide according to claim 10 which the serine residue of SEQ ID NO:6 is replaced by phosphoserine.

14. The kit according to claim 6 wherein the specific binding partner for the phosphorylatable portion of each said substrate polypeptide is the same.

15. The kit according to claim 6, wherein the binding partner has specificity for the phosphorylatable portion, either (i) only when the phosphorylatable portion is phosphorylated; or (ii) only when the phosphorylatable portion is not phosphorylated.

* * * * *

UNITED STATES PATENT AND TRADEMARK OFFICE
CERTIFICATE OF CORRECTION

PATENT NO. : 7,727,950 B2
APPLICATION NO. : 10/510875
DATED : June 1, 2010
INVENTOR(S) : Chris Armstrong et al.

It is certified that error appears in the above-identified patent and that said Letters Patent is hereby corrected as shown below:

Title Page, (Item 57) Abstract, please change "and" to --an--.

In column 1, line 7, please change "kinases" to --kinases.--.

In column 1, line 30, please change "targetting" to --targeting--.

In column 2, line 18, please change "is such" to --such--.

In column 4, line 20 (approx.), please change "NO:3)or" to --NO:3) or--.

In column 4, lines 25-26 (approx.), please change "(SEQ ID NO:2)sequence" to --(SEQ ID NO:6) sequence--.

In column 4, line 48, please change "decending" to --descending--.

In column 6, line 32, please change "(SEQ ID NO:6)but" to --(SEQ ID NO:6) but--.

In column 6, line 33, please change "(SEQ ID NO:7)or" to --(SEQ ID NO:7) or--.

In column 6, line 57, please change "LSPAEPG" to --LSFAEPG--.

In column 7, lines 11-12, please change "Arg-Ala-Arg-Thr-Leu-Ser-Phe-Ala-Glu-Pro-Gly(SEQ ID NO:16)" to --Arg-Ala-Arg-Thr-Leu-Ser-Phe-Ala-Glu-Pro-Gly (SEQ ID NO:16)--.

In column 7, line 16, please change "is(SEQ ID NO:6)" to --(SEQ ID NO:6)--.

In column 7, lines 16-17, please change "phosphoserine(SEQ ID NO:7)." to --phosphoserine (SEQ ID NO:7).--.

In column 8, line 67 - column 9, line 1, please change "Saccaromyces" to --Saccharomyces--.

In column 9, line 24, please change "Ca" to --Cα--.

In column 9, line 67, please change "LSFAEPG(SEQ ID NO:6)." to --LSFAEPG (SEQ ID NO:6).--.

In column 10, line 18, please change "LSFAEPG(SEQ ID NO:6)." to --LSFAEPG (SEQ ID NO:6).--.

In column 10, line 20, please change "kinase" to --kinase.--.

Signed and Sealed this
Eleventh Day of January, 2011

David J. Kappos
*Director of the United States Patent and Trademark Office*

CERTIFICATE OF CORRECTION (continued)

U.S. Pat. No. 7,727,950 B2

In column 10, line 35 (approx.), please change "is invention" to --invention--.

In column 10, line 36 (approx.), please change "farther" to --further--.

In column 11, line 63, please change "fluourescence" to --fluorescence--.

In column 12, line 49, please change "LpSFAEPG(SEQ ID NO:7)." to --LpSFAEPG (SEQ ID NO:7).--.

In column 13, line 23 (approx.), please change "Biochlemistry" to --Biochemistry--.

In column 13, line 63, please change "Linases" to --Kinases--.

In column 14, line 8 (approx.), please change "Linases" to --Kinases--.

In column 14, line 24 (approx.), please change "PKBA," to --PKBα,--.

In column 14, line 47 (approx.), please change "follow." to --follows.--.

In column 14, line 49 (approx.), please change "[y$^{32}$P]ATP" to --[$\gamma^{32}$P]ATP--.

In column 15, line 33 (approx.), please change "Mm" to --mM--.

In column 15, line 43 (approx.), please change "(PKBα, SGK1),LRRASLG" to --(PKBα, SGK1), LRRASLG--.

In column 17, lines 51-52 (approx.), please change "phosphospecifc" to --phosphospecific--.

In column 18, line 13 (approx.), please change "Farner," to -- Farmer,--.

In column 18, line 16 (approx.), please change "807-815" to --807-815.--.

In column 18, line 26 (approx.), please change "95-105" to --95-105.--.

In column 18, line 28 (approx.), please change "Biochim." to --Biochem.--.

In column 18, line 29 (approx.), please change "191-225" to --191-225.--.

In column 18, line 40 (approx.), please change "319-328" to --319-328.--.

In column 33, line 51 (approx.), in claim 6, please change "farther" to --further--.

In column 34, line 37, in Claim 10, please change "kinase," to --kinase--.

In column 34, line 48 (approx.), in Claim 13, please change "which" to --in which--.

SEQUENCE LISTING

<160> NUMBER OF SEQ ID NOS: 31

<210> SEQ ID NO 1
<211> LENGTH: 5
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (4)..(4)
<223> OTHER INFORMATION: Any amino acid

<400> SEQUENCE: 1

Arg Arg Arg Xaa Ser
1               5

<210> SEQ ID NO 2
<211> LENGTH: 6
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: R or K
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (5)..(5)
<223> OTHER INFORMATION: Any amino acid

<400> SEQUENCE: 2

Xaa Xaa Arg Xaa Xaa Ser
1               5

<210> SEQ ID NO 3
<211> LENGTH: 6
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Any bulky hydrophobic residue
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (5)..(5)
<223> OTHER INFORMATION: Any amino acid

<400> SEQUENCE: 3

Xaa Xaa Arg Xaa Xaa Ser
1               5

```
<210> SEQ ID NO 4
<211> LENGTH: 10
<212> TYPE: PRT
<213> ORGANISM: Artificial sequence
<220> FEATURE:
<223> OTHER INFORMATION: Consensus sequence

<400> SEQUENCE: 4

Arg Arg Arg Leu Ser Phe Ala Glu Pro Gly
1               5                   10

<210> SEQ ID NO 5
<211> LENGTH: 5
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Any amino acid
<220> FEATURE:
<221> NAME/KEY: MISC_FEATURE
<222> LOCATION: (2)..(2)
<223> OTHER INFORMATION: Phosphorylated serine
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid

<400> SEQUENCE: 5

Xaa Xaa Xaa Xaa Ser
1               5

<210> SEQ ID NO 6
<211> LENGTH: 7
<212> TYPE: PRT
<213> ORGANISM: Artificial sequence
<220> FEATURE:
<223> OTHER INFORMATION: Consensus sequence

<400> SEQUENCE: 6

Leu Ser Phe Ala Glu Pro Gly
1               5

<210> SEQ ID NO 7
<211> LENGTH: 7
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Phosphorylated serine

<400> SEQUENCE: 7

Leu Xaa Phe Ala Glu Pro Gly
1               5

<210> SEQ ID NO 8
<211> LENGTH: 5
<212> TYPE: PRT
<213> ORGANISM: Artificial sequence
<220> FEATURE:
<223> OTHER INFORMATION: Consensus sequence
```

```
<220> FEATURE:
<221> NAME/KEY: MISC_FEATURE
<222> LOCATION: (1)..(1)
<223> OTHER INFORMATION: Arg or Lys
<220> FEATURE:
<221> NAME/KEY: MISC_FEATURE
<222> LOCATION: (2)..(2)
<223> OTHER INFORMATION: Arg or Lys
<220> FEATURE:
<221> NAME/KEY: MISC_FEATURE
<222> LOCATION: (3)..(3)
<223> OTHER INFORMATION: Arg or Lys
<220> FEATURE:
<221> NAME/KEY: MISC_FEATURE
<222> LOCATION: (4)..(4)
<223> OTHER INFORMATION: Any amino acid

<400> SEQUENCE: 8

Xaa Xaa Xaa Xaa Ser
1               5

<210> SEQ ID NO 9
<211> LENGTH: 6
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Arg or Lys
<220> FEATURE:
<221> NAME/KEY: MISC_FEATURE
<222> LOCATION: (3)..(3)
<223> OTHER INFORMATION: Arg or Lys
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid
<220> FEATURE:
<221> NAME/KEY: MISC_FEATURE
<222> LOCATION: (5)..(5)
<223> OTHER INFORMATION: Any amino acid

<400> SEQUENCE: 9

Xaa Xaa Xaa Xaa Xaa Ser
1               5

<210> SEQ ID NO 10
<211> LENGTH: 11
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid

<400> SEQUENCE: 10

Tyr Xaa Thr Xaa Leu Ser Phe Ala Glu Pro Gly
1               5                   10

<210> SEQ ID NO 11
<211> LENGTH: 11
```

```
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Any bulky hydrophobic residue
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(4)
<223> OTHER INFORMATION: any amino acid

<400> SEQUENCE: 11

Xaa Xaa Tyr Xaa Leu Ser Phe Ala Glu Pro Gly
1               5                   10

<210> SEQ ID NO 12
<211> LENGTH: 10
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (2)..(2)
<223> OTHER INFORMATION: Phosphorylated serine

<400> SEQUENCE: 12

Xaa Xaa Xaa Leu Ser Phe Ala Glu Pro Gly
1               5                   10

<210> SEQ ID NO 13
<211> LENGTH: 13
<212> TYPE: PRT
<213> ORGANISM: Artificial sequence
<220> FEATURE:
<223> OTHER INFORMATION: Consensus sequence

<400> SEQUENCE: 13

Lys Lys Leu Asn Arg Thr Leu Ser Phe Ala Glu Pro Gly
1               5                   10

<210> SEQ ID NO 14
<211> LENGTH: 7
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: phosphoserine

<400> SEQUENCE: 14

Leu Xaa Phe Ala Glu Pro Gly
1               5

<210> SEQ ID NO 15
```

```
<211> LENGTH: 9
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Phosphoserine

<400> SEQUENCE: 15

Leu Xaa Ser Pro Ala Glu Pro Gly Cys
1               5

<210> SEQ ID NO 16
<211> LENGTH: 11
<212> TYPE: PRT
<213> ORGANISM: Artificial sequence
<220> FEATURE:
<223> OTHER INFORMATION: Consensus sequence

<400> SEQUENCE: 16

Arg Ala Arg Thr Leu Ser Phe Ala Glu Pro Gly
1               5                   10

<210> SEQ ID NO 17
<211> LENGTH: 8
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Phosphoserine

<400> SEQUENCE: 17

Leu Xaa Phe Ala Glu Pro Gly Cys
1               5

<210> SEQ ID NO 18
<211> LENGTH: 11
<212> TYPE: PRT
<213> ORGANISM: Artificial sequence
<220> FEATURE:
<223> OTHER INFORMATION: Consensus sequence

<400> SEQUENCE: 18

Gly Arg Pro Arg Thr Ser Ser Phe Ala Glu Gly
1               5                   10

<210> SEQ ID NO 19
<211> LENGTH: 7
<212> TYPE: PRT
<213> ORGANISM: Artificial sequence
<220> FEATURE:
<223> OTHER INFORMATION: Consensus sequence

<400> SEQUENCE: 19

Leu Arg Arg Ala Ser Leu Gly
1               5

<210> SEQ ID NO 20
<211> LENGTH: 32
<212> TYPE: PRT
<213> ORGANISM: Artificial sequence
<220> FEATURE:
<223> OTHER INFORMATION: Consensus sequence
```

-continued

```
<400> SEQUENCE: 20

Lys Glu Ala Lys Glu Lys Arg Gln Glu Gln Ile Ala Lys Arg Arg Arg
1               5                   10                  15

Leu Ser Ser Leu Arg Ala Ser Thr Ser Lys Ser Gly Gly Ser Gln Lys
            20                  25                  30

<210> SEQ ID NO 21
<211> LENGTH: 10
<212> TYPE: PRT
<213> ORGANISM: Artificial sequence
<220> FEATURE:
<223> OTHER INFORMATION: Consensus sequence

<400> SEQUENCE: 21

Lys Lys Leu Asn Arg Thr Leu Ser Val Ala
1               5                   10

<210> SEQ ID NO 22
<211> LENGTH: 10
<212> TYPE: PRT
<213> ORGANISM: Artificial sequence
<220> FEATURE:
<223> OTHER INFORMATION: Consensus sequence

<400> SEQUENCE: 22

Lys Lys Leu Arg Arg Thr Leu Ser Val Ala
1               5                   10

<210> SEQ ID NO 23
<211> LENGTH: 23
<212> TYPE: PRT
<213> ORGANISM: Artificial sequence
<220> FEATURE:
<223> OTHER INFORMATION: Consensus sequence

<400> SEQUENCE: 23

Lys Lys Lys Val Ser Arg Ser Gly Leu Tyr Arg Ser Pro Ser Met Pro
1               5                   10                  15

Glu Asn Leu Asn Arg Pro Arg
            20

<210> SEQ ID NO 24
<211> LENGTH: 15
<212> TYPE: PRT
<213> ORGANISM: Artificial sequence
<220> FEATURE:
<223> OTHER INFORMATION: Consensus sequence

<400> SEQUENCE: 24

His Met Arg Ser Ala Met Ser Gly Leu His Leu Val Lys Arg Arg
1               5                   10                  15

<210> SEQ ID NO 25
<211> LENGTH: 11
<212> TYPE: PRT
<213> ORGANISM: Artificial sequence
<220> FEATURE:
<223> OTHER INFORMATION: Consensus sequence

<400> SEQUENCE: 25

Met His Arg Gln Glu Thr Val Asp Cys Leu Lys
1               5                   10

<210> SEQ ID NO 26
<211> LENGTH: 11
```

```
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (6)..(6)
<223> OTHER INFORMATION: Phosphoserine

<400> SEQUENCE: 26

Arg Ala Arg Thr Leu Xaa Phe Ala Glu Pro Gly
1               5                   10

<210> SEQ ID NO 27
<211> LENGTH: 10
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (5)..(5)
<223> OTHER INFORMATION: Phosphoserine

<400> SEQUENCE: 27

Arg Arg Arg Leu Xaa Phe Ala Glu Pro Gly
1               5                   10

<210> SEQ ID NO 28
<211> LENGTH: 4
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Thr or Asn

<400> SEQUENCE: 28

Pro Pro Xaa Lys
1

<210> SEQ ID NO 29
<211> LENGTH: 11
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(4)
<223> OTHER INFORMATION: any amino acid

<400> SEQUENCE: 29

Arg Xaa Arg Xaa Leu Ser Phe Ala Glu Pro Gly
1               5                   10

<210> SEQ ID NO 30
<211> LENGTH: 11
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
```

-continued

```
<223> OTHER INFORMATION: Any bulky hydrophobic residue
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(4)
<223> OTHER INFORMATION: any amino acid

<400> SEQUENCE: 30

Xaa Xaa Arg Xaa Leu Ser Phe Ala Glu Pro Gly
1               5                   10

<210> SEQ ID NO 31
<211> LENGTH: 13
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (8)..(8)
<223> OTHER INFORMATION: Phosphoserine

<400> SEQUENCE: 31

Lys Lys Leu Asn Arg Thr Leu Xaa Phe Ala Glu Pro Gly
1               5                   10
```